| United States Patent [19] | [11] Patent Number: 5,250,695 |
|---|---|
| Blatt et al. | [45] Date of Patent: Oct. 5, 1993 |

[54] USE OF SPECIFIC COUNTERANIONS TO MODIFY THE SOLUBILITY OF TETRAZOLIUM SALTS

[75] Inventors: Joel M. Blatt, Granger; Robert P. Hatch, Elkhart, both of Ind.

[73] Assignee: Miles Inc., Elkhart, Ind.

[21] Appl. No.: 898,317

[22] Filed: Jun. 15, 1992

[51] Int. Cl.$^5$ .................. C07D 417/04; C07D 257/04
[52] U.S. Cl. .................... 548/150; 548/162; 548/198; 548/250
[58] Field of Search ............... 548/250, 162, 198, 150

[56] References Cited

U.S. PATENT DOCUMENTS

| 1,892,019 | 12/1932 | Stoll et al. | 546/44 |
|---|---|---|---|
| 3,655,382 | 4/1972 | Brault et al. | 96/48 |
| 4,221,864 | 9/1980 | Iytaka et al. | 430/57 |
| 4,334,071 | 6/1982 | Kotick et al. | 546/74 |
| 5,013,647 | 5/1991 | Town et al. | 548/250 |

Primary Examiner—Joseph Paul Brust
Assistant Examiner—MarySusan H. Gabilan
Attorney, Agent, or Firm—Jerome L. Jeffers

[57] ABSTRACT

Disclosed are sulfonate and phosphonate salts of tetrazolium compounds whose enhanced solubility in various solvents renders them particularly suitable for use as redox indicators in dry reagent, diagnostic test systems.

10 Claims, No Drawings

USE OF SPECIFIC COUNTERANIONS TO MODIFY THE SOLUBILITY OF TETRAZOLIUM SALTS

BACKGROUND OF THE INVENTION

Tetrazolium salts, such as 2-(4-iodophenyl)-3-(4-nitrophenyl)-5-phenyl tetrazolium (INT), are very useful in the measurement of analytes which can be converted to an equivalent concentration of NADH due to the reduction of the tetrazolium salt to its corresponding formazan which reduction can be accurately measured by colorimetric means.

A typical reagent system for determining glucose concentration in body fluids is based on reductive chemistry wherein the primary components are hexokinase (HK), adenosine triphosphate (ATP), glucose-6-phosphate dehydrogenase (G-6-PDH), diaphorase, nicotinamideadenine dinucleotide (AND) and a tetrazolium salt as indicator. In operation, hexokinase catalyzes the reaction in which, in the presence of glucose, a phosphate radical is taken from ATP thereby converting it to adenosine diphosphate to form glucose-6-phosphate which is oxidized in the presence of AND and G-6-PDH thereby reducing AND to NADH. The NADH, in the presence of diaphorase as electron acceptor, reduces the colorless tetrazolium salt to its colored formazan counterpart thereby providing a detectable response. The reaction steps, as represented by the following scheme, represent the determination of NADH as an indirect means of determining the glucose concentration in the test sample:

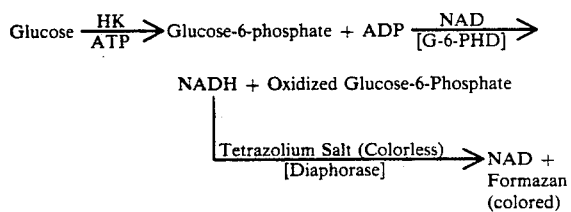

The utility of tetrazolium salts in such systems for detecting such analytes is proportional to their solubility in water or suitable organic solvents. This is particularly true in the case of dry reagent diagnostic test devices, such as those in which a tetrazolium salt is dissolved in a polar organic solvent for impregnation into a carrier matrix such as paper or a polymer matrix or dissolved in an aqueous solution of a film forming polymer such as gelatin. Tetrazolium salt indicators are typically used with gelatin film and other dry reagent formulations which employ diaphorase or a chemical mediator in the color generating step. An adequate amount of indicator must be present to completely consume the reducing equivalents that originate from the influx of an analyte such as glucose. In most cases, in order to obtain a reasonably thin coating of the film forming polymer and to provide a sufficient supply of the indicator within the porous matrix, the concentration of indicator must be in the range of 0.05M to 0.15M or more.

U.S. Pat. No. 1,892,019 discloses the increased water solubility of benzylmorphine after it is reacted with alkyl sulphonic acid, e.g. methane or ethanesulfonic acid, by formation of the corresponding salt. U.S. Pat. No. 4,334,071 discloses the enhancement of the solubility of 17-cyclobutylmethyl-3-hydroxy-862-methyl-6-methylene morphinane by converting its chloride salt to the corresponding methanesulfonate.

U.S. Pat. No. 3,655,382 discloses tetrazolium thiazolium salts in which the counteranion can be chloride, iodide, bromide, thiocyanate, thiosulfate, sulfate, paratoluenesulfonate, methylsulfate, ethyl sulfate, nitrate, acetate, perchlorate, perborate, sulfite, hydroxide or carbonate.

In U.S. Pat. No. 4,221,864 the patentees state that one of the objects of their invention is to provide a novel light sensitive photographic material containing a tetrazolium compound. They point out that this and other objects can be attained by preparing a photographic material which comprises a support and at least one light sensitive silver halide layer and another hydrophylic colloidal layer coated on the support, one of which layer contains a tetrazolium salt. They point out that where the salt of a tetrazolium compound is used as a non-diffusible ingredient, such a salt can be synthesized by reacting a tetrazolium cation with an anion capable of making the selected compound non-diffusible. Counteranions such as those derived from higher alkylbenzenesulfonic acids, e.g. dodecylbenzenesulfonic acid or a higher alkyl sulfuric acid ester such as lauryl sulfate are disclosed.

SUMMARY OF THE INVENTION

The present invention involves certain salts of tetrazolium compounds which exhibit unexpectedly high solubility in polar solvents. These salts include a counteranion of the formula:

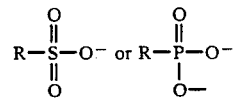

In the above formula, R is an organic radical suitable for increasing the solubility of the tetrazolium salt in an aqueous or non-aqueous polar solvent. Preferably, R is a straight or branched chain alkyl of 1 to 7 carbon atoms or phenyl.

Also included within the scope of this invention is a diagnostic test device comprising a reagent system incorporated into a carrier matrix containing one or more of the sulfonate and/or phosphonate tetrazolium salts.

DESCRIPTION OF THE INVENTION

The tetrazolium salts of the present invention can be represented by the formula:

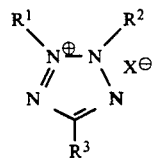

wherein $X^\ominus$ is the counteranion as defined above, $R^1$ and $R^3$ are phenyl groups and $R^2$ is phenyl or 2-thiazolyl. The phenyl and optional thiazol groups can be substituted or unsubstituted. More specifically, $R^1$, $R^3$ and optionally $R^2$ can be represented by, but are not limited to, the formula:

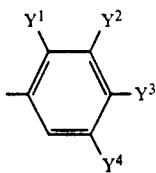

wherein the Y groups ($Y^1$, $Y^2$, $Y^3$ or $Y^4$) which are the same or different can be, for example, alkoxy, aryloxy, alkyl, amido, alkylamido, arylamido, alkylthio, arylthio, halo, hydrogen, hydroxy, carbamoyl, carbalkoxy, carboxyl, cyano, nitro, sulfo, sulfonamido, sulfamoyl, trialkylamino amino or ureido groups.

When $R_2$ is a thiazole group, it can be unsubstituted or substituted. For example, where the thiazole group is represented by the formula:

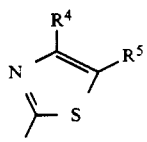

where $R^4$ and $R^5$ are hydrogen or some other substitutent.

In a preferred embodiment of the present invention, the $R^1$ and $R^3$ moieties of the tetrazolium salt are as described above and $R^2$ is a thiazole group in which $R^4$ and $R^5$ together form a benzo ring which is substituted or unsubstituted; $R^4$ is carboxyl, carbalkoxy, carbamoyl, or cyano and $R^5$ is alkyl or chloro; $R^4$ is alkyl or aryl and $R^5$ is carboxyl, carbalkoxy, carbaryloxy, carbamoyl or cyano; $R^4$ is di- or trifluoroalkyl wherein the fluoro substituents are on the carbon adjacent to the thiazolyl residue; or one or both of $R^4$ and $R^5$ are substituted or unsubstituted phenyl, and if only one is substituted phenyl, the other is hydrogen or alkyl. Among those tetrazolium cations which are particularly useful in the context of the present invention are those in which $R^4$ and $R^5$ together form a benzo ring to give a benzothiazole residue having the formula:

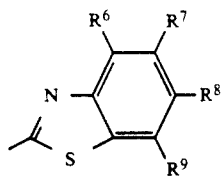

wherein (i) $R^6$ and $R^7$ or $R^7$ and $R^8$ or $R^8$ and $R^9$ together form a benzo or cyclohexyl ring that is unsubstituted or substituted with alkoxy, aryloxy, alkyl, amido, alkylamido, arylamido, alkylthio, arylthio, amino, carbamoyl, carbalkoxy, cyano, halo, hydroxyl, sulfo, sulfonamido, sulfamoyl, trialkylammonio, or ureido, and wherein the others, same or different, are hydrogen, alkoxy, aryloxy, alkyl, amido, alkylamido, arylamido, alkylthio, arylthio, amino, carbamoyl, carbalkoxy, cyano, halo, hydroxyl, sulfo, sulfonamido, sulfamoyl, trialkylammonio, or ureido, provided that where $R^7$ and $R^8$ together form a benzo or cyclohexyl ring, $R^6$ is not hydrogen, or (ii) one or more of $R^6$, $R^7$, $R^8$, and $R^9$ is alkoxy, aryloxy, alkyl, amido, alkylamido, arylamido, alkylthio, arylthio, amino, carbamoyl, carbalkoxy, cyano, halo, hydroxyl, sulfo, sulfonamido, sulfamoyl, trialkylammonio, or ureido, and the others, if any, are hydrogen.

The salts of the present invention are most conveniently prepared by interaction of less soluble salts of the tetrazolium compound with an anion exchange resin which is converted to its alkyl or benzene sulfonate or phosphonate form. This procedure is preferably carried out in the presence of an ion exchange resin due to the ease of purification which is rendered by this technique. Thus, by using the ion exchange resin one can simply stir the tetrazolium salt in a slurry of the resin followed by filtration, concentration and crystallization to obtain the pure salt. Alternative procedures which involve stirring the less soluble tetrazolium salt with the alkyl or benzene sulfonic or phosphoric acid or their salts can also be employed. However, when an ion exchange resin is used the excess sulfonate or phosphate tetrazolium salt is attached to the resin and can be separated from the reaction mass by filtration.

The following examples illustrate the general procedure for preparation of the tetrazolium salts of the present invention and their inclusion in analytical test devices. EXAMPLE I A. Preparation of ion exchange resin ($RSO_3^-$ form).

Sulfonic acid is added to 20 g of Amberlite IRA-400 (—OH) ion exchange resin in 60 mL of water until a pH of 1.5 is achieved. The mixture is filtered and washed with 100 mL of water followed by a second washing with 100 mL of methanol.

B. Preparation of tetrazolium sulfonates.

A slurry of 5.5 g of tetrazolium salt, e.g. the tetrafluoroborate, and 50 g of moist resin is stirred in 300 mL of methanol for 2–4 hours. In cases where the tetrazolium salt's poor solubility inhibits the exchange, the mixture is warmed to 40° C. The mixture is filtered and then concentrated to a gum like residue whereupon the product precipitates after stirring with ethyl acetate.

C. Preparation of tetrazolium bromides.

A slurry of 2 g of the tetrazolium tetrafluoroborate is stirred overnight with 50 mL of 48% hydrobromic acid. The mixture is then filtered and washed with 200 mL of water to yield the tetrazolium bromide.

D. Preparation of tetrazolium tetrafluoroborates.

These salts are prepared by stirring the appropriate formazan with isoamylnitrate in the presence of 48% fluoroboric acid in acetic acid and filtering the product. Optionally, if the product does not precipitate, ether is added to force precipitation. Nitrate salts are prepared in a similar manner in the absence of fluoroboric acid.

E. Solubility testing.

Approximately 10 mg of the tetrazolium salt is measured out and the solvent added in increments of 25 μL until the salt dissolves. When it becomes apparent that a particular compound is only marginally soluble, the volume of solvent increments is increased to 50 and then to 100 μL.

The results of this solubility testing are set out in Table I in which the following abbreviations are used:

INT: 2-(4-iodophenyl)-3-(4-nitrophenyl)-5-phenyl tetrazolium

MTT: [3-(4,5-dimethylthiazol-2-yl)-2,5-diphenyl tetrazolium

DCT: 2-(4-difluoromethyl-5-chlorothiazol-2-yl)-3-(3,4,5-trimethoxyphenyl)-5-(3,4-methylenedioxyphenyl) tetrazolium DCMT: 2-(4-difluoromethyl-5-chlorothiazol-2-yl)-3-(2 methoxyphenyl)-5-(3,4-methylenedioxyphenyl) tetrazolium MTM: 2-(5-methoxynaphtho[1,2-d]thiazol-2-yl)-3-(3,4,5-trimethoxyphenyl)-5-(4-methoxyphenyl) tetrazolium Me: methyl
Et: ethyl
Pr: propyl
Bu: butyl
Pe: pentyl
Bz: benzene

TABLE I

| Compound | mp (°C.) | Solubility (m mol L) | |
|---|---|---|---|
| | | Methanol | Water |
| INT Cl$^-$ | | | 3 |
| INT MeSO$_3^-$ | 132-135 | | 35 |
| MTT Br$^-$ | | 360 | 18 |
| MTT MeSO$_3^-$ | 189-193 | 1150 | >1,000 |
| DCT Br$^-$ | 189-191 | 10 | <1 |
| DCT BF$_4^-$ | 239-241 | <16 | <0.5 |
| DCT NO$_3^-$ | 184-185 | 22 | 2 |
| DCT MeSO$_3^-$ | 129-131 | >500 | 73 |
| DCT EtSO$_3^-$ | 157-159 | >600 | 26 |
| DCT PrSO$_3^-$ | 174-176 | >650 | 16 |
| DCT BzSO$_3^-$ | 175-177 | >550 | |
| DCMT Br$^-$ | 167-169 | 24 | <1 |
| DCMT BF$_4^-$ | 231-233 | 12.9 | 2.7 |
| DCMT MeSO$_3^-$ | 170-179 | >760 | 248 |
| DCMT PrSO$_3^-$ | 176-168 | >760 | 23 |
| DCMT BuSO$_3^-$ | 183-185 | >700 | 15 |
| DCMT PeSO$_3^-$ | 198-200 | >700 | 2.6 |
| MTM NO$_3^-$ | 251-252 | 7.6 | |
| MTM MeSO$_3^-$ | 257-258 | 48 | |
| MTM PrSO$_3^-$ | 241-141 | 100 | |
| MTM BzSO$_3$ | 251-251 | 19 | |

From the data tabulated in Table I it can be determined that the conversion of the chloride salt of INT to its methanesulfonate increased its water solubility by a factor of greater than 10. The conversion of MTT bromide to the methane sulfonate provides an even greater increase in water solubility as well as increasing the salt's solubility in methanol. In the case of DCT, the bromide, tetrafluoroborate and nitrate salts are only marginally soluble in water and methanol whereas the methanesulfonate is highly soluble in both. As the size of the alkyl group increases, the water solubility decreases whereas solubility in methanol increases. The enhanced water solubility of these salts is significant since it facilitates the inclusion of adequate quantities of the tetrazolium salt into thin films of water soluble polymers such as gelatin. The high methanol solubility of the benzenesulfonate is also significant. The use of non-aqueous solvents in preparing the previously mentioned carrier matrix films is important because it enables one to deposit the indicator into the matrix from non-aqueous solutions wherein the liquid phase is a non-solvent for the reagent system used to create the detectable response. Typical carrier matrixes include bibulous materials such as filter paper or a nonbibulous material such as a membrane of a polymerized substance or a combination thereof. Accordingly, it is significant that methanol solubility of MTM is substantially increased by converting it to the methane- or propanesulfonate. The solubility of this tetrazolium compound decreases when it is converted to the benzenesulfonate but is still substantially greater than the nitrate. Conversely, no improvement in methanol solubility was observed for the paratoluene and naphthalene salts of these tetrazolium compounds.

Further reference to Table I reveals that the water and methanol solubility of DCMT is greatly enhanced by conversion of the bromide or tetrafluoroborate salts to the corresponding methanesulfonate. As the length of the alkyl chain increases, water solubility declines while methanol solubility remains substantially unchanged.

The tetrazolium salts of the present invention are particularly suitable for use in analytical test devices of the type previously mentioned since the solubility of the salt can be tailored to the particular device being fabricated. For example if it is desired to impregnate a carrier matrix or a gelatin film with the tetrazolium salt from an aqueous solution, the organic moiety, R in the foregoing general formula, is lower alkyl, preferably methyl, in order to provide a tetrazolium salt with the requisite hydrophilic properties. In the manufacture of analytical devices where it is desirable to apply the various reagents from a solution other than that from which the tetrazolium salt is applied, the R group is selected to render the salt soluble in polar organic solvents, which are not good solvents for the other reagents, to facilitate application of the tetrazolium indicator from its solution in the polar organic solvent either before or after the other reagents have been applied to the substrate from their aqueous solution. In this manner premixing of the reagent system and the tetrazolium salt in a single solvent system can be avoided by tailoring the counteranion to the solvent system of choice. Methanol is a particularly good solvent for certain tetrazolium indicators wherein the R group in the counteranion is phenyl.

The preparation of a polymer matrix, analytical device using a tetrazolium salt of the present invention is illustrated by the following example. EXAMPLE II An 80 millimole/liter solution of 2-(4-difluoromethyl-5-chlorothiazol-2-yl)-3-(3,4,5 trimethoxyphenyl)-(5-(3,4-methylenedioxyphenyl) tetrazolium benzenesulfonate in methanol containing 0.75% Cremophor surfactant was prepared. A 500 foot strip of a 6 mil thick, 8.625 inch wide, zwitterionic charged nylon fabric was impregnated with 4 liters of the tetrazolium salt solution to cause saturation. Extraction of the fabric with methanol and determination of the indicator's concentration by HPLC spectroscopy indicated that it was present in the fabric at a concentration of 4–5μ mole/in$^2$. After drying, the strip was treated with 5 ½liters of an aqueous solution containing 100 mM/L adenosine triphosphate. After the aqueous impregnation, 1 liter of the aqueous solution remained which was found to contain 3 mM of the tetrazolium salt which was extracted from the treated membrane. The solution also contained some formazan which was not quantified. Assuming that the formazan was also 3 mM, there was recovered an equivalent of 6 millimoles of the tetrazolium salt which had been extracted from the membrane during the aqueous impregnation, representing a loss of 1.875 percent.

4 L×0.08 moles/L=0.32 moles of tetrazolium salt impregnated into the membrane during first treatment.

1 L×0.006 moles/L=0.006 moles extracted during aqueous impregnation.

$$\frac{0.006}{0.320} = 1.875\%$$

The amount of ATP in the membrane was determined to be between 82 and 92% of the theoretical level.

Impregnation of the fabric with methanolic, ethanolic or other alcoholic solutions of the indicator in which the counteranion was nitrate or tetrafluoroborate was unsuccessful due to the low solubility of these salts in alcohol. Concentrations of these salts comparable to that achieved with methanol was achieved using a 1:1 mixture of dimethylformamide and methanol. However, the use of dimethylformamide is undesirable on an industrial manufacturing scale since it is an established liver and kidney toxin. Furthermore, application of the tetrazolium salt from its methanol solution facilitates the use of a two dip procedure for applying the indicator in a first dip with the enzymes and other water soluble constituents of the reagent system in a second dip from their aqueous solutions without rehydrating the already deposited tetrazolium salt. By selecting a more hydrophilic organic radical, such as that of methanesulfonate, the tetrazolium salt is rendered water soluble so that the entire reagent system including the indicator can be applied in a single dip. Application from separate dips as in this example is preferred in order to minimize interaction between the reagents during the application of the reagent system to the substrate.

While the foregoing data illustrate the enhanced solubility of alkyl and benzenesulfonates, similar results can be achieved with the corresponding phosphonate salts. This is the case because the oxygen atoms on the phosphorous group improve water solubility through hydrogen bonding in a manner similar to those on the sulfonate. The organic group on the phosphonates is analogous to the alkyl or phenyl group of the sulfonates and can be manipulated in a similar manner to aid in the salt's solubility in various solvents.

What is claimed is:

1. Sulfonate and phosphonate salts of tetrozolium compounds wherein the anion is represented by the formula:

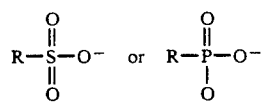

wherein R is a straight or branched alkyl group of from 1 to 7 carbon atoms or phenyl.

2. The tetrazolium salts of claim 1 wherein the tetrazolium salt is represented by the formula

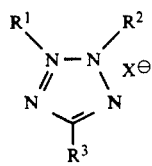

wherein $X^\ominus$ is the counter anion, $R^1$ and $R^2$ are phenyl groups and $R^2$ is phenyl or 2-thiazolyl wherein the phenyl groups are unsubstituted or substituted as represented by the formula

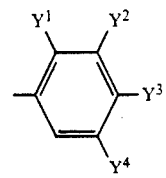

wherein the Y groups, which can be the same or different, are alkoxy, aryloxy, alkyl, amido, alkylamido, arylamido, alkylthio, arylthio, halo, hydrogen, hydroxy, carbamoyl, carbalkoxy, carboxyl, cyano, nitro, sulfo, sulfonamido, sulfanoyl, trialkylamino or ureido.

3. The tetrazolium salts of claim 1 wherein the anion is

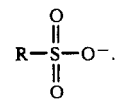

4. The tetrazolium salts of claim 2 wherein $R^2$ is substituted or unsubstituted thiazol characterized by the formula:

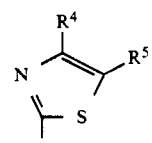

wherein $R^4$ and $R^5$ together form a benzo ring which is substituted or unsubstituted or $R^4$ is hydrogen, carboxyl, carbalkoxy, carbamoyl, or cyano and $R^5$ is hydrogen, alkyl or chloro or $R^4$ is alkyl or aryl and $R^5$ is carboxyl, carbalkoxy, carbaryloxy, carbamoyl or cyano or $R^4$ is di- or trifluoroalkyl wherein the fluoro substituents are on the carbon adjacent to the thiazole residue; or one or both of $R^4$ and $R^5$ are substituted phenyl and if only one is substituted phenyl, the other is hydrogen or alkyl.

5. The tetrazolium salts of claim 4 wherein $R^4$ is difluoromethyl and $R^5$ is chloro.

6. The tetrazolium salts of claim 4 wherein $R^4$ and $R^5$ together form a benzo ring to provide a benzthiazole residue having the formula:

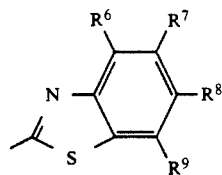

wherein (i) $R^6$ and $R^7$ or $R^7$ and $R^8$ or $R^8$ and $R^9$ together form a benzo or cyclohexyl ring that is unsubstituted or substituted with alkoxy, aryloxy, alkyl, carbamoyl, carbalkoxy, cyano, halo, hydroxyl, sulfo, sulfonamido, sulfamoyl, trialkylamino or ureido and where the others, which can be the same or different, are hydrogen, alkoxy, arloxy, alkyl, amido, alkylamido, arylamido, alkylthio, arylthio, amino, carbamoyl, carbalkoxy, cyano, halo, hydroxyl, sulfo, sulfonamido, sulfamoyl, trialkylamino or ureido provided that when $R^7$ and $R^8$ together form a benzo or cyclohexyl ring, $R^6$ is not hydrogen, or (ii) one or more of $R^6$, $R^7$, $R^8$ is alkoxy, aryloxy, alkyl, amido, alkylamido, arylamido, alkylthio, hydroxyl, sulfo, sulfonamido, sulfamoyl, trialkylamino or ureido.

7. A tetrazolium salt as characterized in claim 1 which is 2-(4-difluoromethyl-5-chlorothiazol-2-yl)-3-(2-methoxyphenyl)-5-(3,4-methylenedioxyphenyl) teterazolium salt.

8. A tetraolium salt as characterized by claim 1 which is 2-(4-difluoromethyl-5-chlorothiazol-2-yl)-3-(3,4,5-trimethoxyphenyl)-5-(3,4-methylenedioxyphenyl) tetrazolium salt.

9. The tetrazolium salts of claim 3 wherein R is phenyl.

10. 2-(4-difluoromethyl-5-chlorothiazol-2-yl)-2,5-diphenyl tetrazolium benzene sulfonate.

* * * * *